(12) United States Patent
Xie et al.

(10) Patent No.: US 10,463,735 B2
(45) Date of Patent: Nov. 5, 2019

(54) METHOD AND APPARATUS FOR ADJUSTING CORNEAL CURVATURE THROUGH DIGITAL CORNEAL CROSSLINKING

(71) Applicant: ZHEJIANG UNIVERSITY, Hangzhou, Zhejiang Province (CN)

(72) Inventors: Tao Xie, Hangzhou (CN); Jingjun Wu, Hangzhou (CN); Qian Zhao, Hangzhou (CN); Limei Huang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 276 days.

(21) Appl. No.: 15/352,467

(22) Filed: Nov. 15, 2016

(65) Prior Publication Data

US 2018/0050104 A1 Feb. 22, 2018

(30) Foreign Application Priority Data

Aug. 17, 2016 (CN) .......................... 2016 1 0681183

(51) Int. Cl.
| | | |
|---|---|---|
| *A61K 41/00* | (2006.01) | |
| *A61F 9/008* | (2006.01) | |
| *A61B 3/107* | (2006.01) | |
| *A61B 3/113* | (2006.01) | |
| *A61F 9/00* | (2006.01) | |
| *A61F 9/007* | (2006.01) | |
| *A61K 9/00* | (2006.01) | |
| *A61K 9/08* | (2006.01) | |
| *A61K 47/36* | (2006.01) | |

(52) U.S. Cl.
CPC .......... *A61K 41/0057* (2013.01); *A61B 3/107* (2013.01); *A61B 3/113* (2013.01); *A61F 9/008* (2013.01); *A61F 9/0008* (2013.01); *A61F 9/0079* (2013.01); *A61K 9/0048* (2013.01); *A61K 9/08* (2013.01); *A61K 47/36* (2013.01); *A61F 2009/00865* (2013.01); *A61F 2009/00872* (2013.01)

(58) Field of Classification Search
CPC ................ A61K 41/0057; A61F 9/008; A61F 2009/00865; A61F 2009/00872; A61F 9/0079; A61F 9/0008; A61B 3/107; A61B 3/113
See application file for complete search history.

(56) References Cited

U.S. PATENT DOCUMENTS

| | | | | |
|---|---|---|---|---|
| 2010/0226997 | A1* | 9/2010 | Bowman | A61K 9/0048 424/501 |
| 2012/0083772 | A1* | 4/2012 | Rubinfeld | A61F 9/0079 606/4 |
| 2012/0310141 | A1* | 12/2012 | Kornfield | A61F 9/008 604/20 |

\* cited by examiner

*Primary Examiner* — Nathan R Price
*Assistant Examiner* — Anh Bui
(74) *Attorney, Agent, or Firm* — Jiwen Chen

(57) ABSTRACT

The present disclosure concerns a digital corneal crosslinking technology for adjusting the corneal curvature, comprising the following steps: administering in drops a composition comprising a photoinitiator compound to the corneal stromal of the subject, locally irradiating the corneal by utilizing digital micromirror device controlled by computer. The corneal curvature can be adjusted totally or locally. The invention also discloses an apparatus for the digital corneal crosslinking. The method and apparatus is minimum invasive and can be used to accurately and efficiently adjust the corneal curvature.

10 Claims, 2 Drawing Sheets

METHOD AND APPARATUS FOR ADJUSTING CORNEAL CURVATURE THROUGH DIGITAL CORNEAL CROSSLINKING

This application claims the priority benefit of Chinese Application No. 201610681183.7, filed Aug. 17, 2016, which is hereby incorporated by reference.

TECHNICAL FIELD

The present invention generally relates to the field for adjusting corneal curvature and, more particularly, to a method and apparatus for a digital corneal crosslinking technology adjusting the corneal curvature.

BACKGROUND TECHNOLOGY

The corneal is a transparent dioptric media without vascular tissue. It is the most effective refractive surface of the eye optical system and accounts for approximately 70% of the eye's total refractive power. The refractive power of the corneal depends on its curvature and refractive index. Inappropriate refractive power leads to the loss of ability to focus images on the retina, called refractive error, or ametropia. Human eyes often exhibit three kinds of ametropia, including myopia, hyperopia and astigmatism, all of which are caused by an imperfection in the refractive function of the eye. Myopia, commonly known as near-sightedness, is a condition of the eye where the light that comes in does not directly focus on the retina but in front of it. The situation of hyperopia is the opposite to that of myopia. People who has astigmatism usually has a slightly irregular corneal, leading to more than one focus before or behind the retina. The method of surgical correction for ametropia, according to international standards, can be divided into corneal surgery, crystal surgery, and sclera surgery according to the different surgical sites.

The corneal refractive surgery generally includes LASIK (Laser-Assisted In-Situ Keratomileusis) and LASEK (Laser-Assisted Subepithelial Keratomileusis). In correcting myopia, the central stromal layer of the corneal is cut by laser. As a result, the overall corneal curvature is reduced, the refractive power is reduced, so the focus moves to the retina and the patient's vision is corrected. In the case of hyperopia, the peripheral stromal layer is cut to increase the overall curvature. The correction of astigmatism is a little complicated, because the curvature should be adjusted locally.

LASIK is the mainstream method to treat the refractive errors, but it is an invasive process, and often accompanied by some complications.

SUMMARY OF THE INVENTION

The object of the present invention is to overcome the shortcomings of the existing technology, providing a digital corneal crosslinking method and apparatus to adjust the corneal curvature. The disclosed method is minimum invasive and can be used to accurately and efficiently adjust the corneal curvature.

The technical approach provided by the present disclosure is:

A digital corneal crosslinking method to adjust the corneal curvature wherein a composition comprising a photoinitiator compound is administered to the corneal stromal of the subject, and the corneal is selectively and locally irradiated by utilizing digital micromirror device (DMD) controlled by a computer, whereby the corneal curvature is altered.

The digital corneal crosslinking (DCCL) method disclosed above is derived from the existing corneal crosslinking (CCL). Corneal crosslinking is a surgical treatment for corneal ectasia such as keratoconus. It involves a one-time application of riboflavin solution to the eye that is activated by illumination with UV-A light. The riboflavin causes new bonds to form across adjacent collagen strands in the stromal layer of the corneal, which recovers and preserves some of the cornea's mechanical strength.

The technology characteristics of the disclosed digital corneal crosslinking is the digitally controlling the light to achieve the local irradiation of the corneal through computer graphic software loading graphic files. The core part is the digital micromirror device that integrates specified wavelength light source. The digital micromirror device chip is composed of million pieces of microlens of 14*14 microns in size. Each microlens can rapidly spin under computer program control, and its rotational angle determines whether the corresponding micro area is exposed or not. CAD or other graphic software can control the digital micromirror device chip to determine the irradiation area and time.

The local light exposure area and time on the corneal can be determined through corneal biomechanical simulation. On one hand, the simulation is essential to establish the dynamic model of the crosslinking reaction between the photoinitiator and the stromal under irradiation, and determine the relation between the irradiation time and crosslinking density. On the other hand, using corneal biomechanics analyzer can obtain the biomechanical data including corneal thickness, intraocular pressure and so on, and set up the mechanical model. Finite element analysis can be applied to obtain the internal stress distribution for a certain corneal curvature change, and finally the crosslinking density distribution can be also obtained.

The basic principle of digital corneal crosslinking is as follows: the photoinitiator is excited into the triplet state under the irradiation of specific wavelength. Reactive oxygen species including singlet oxygen, ultra oxygen anion, $H_2O_2$ are produced and interact with different molecules, inducing the chemical covalent crosslinking between amino groups of the collagen fibers in the corneal stromal, increasing the crosslinking density of the corneal stromal. The specific light irradiates the local regions of the corneal. Only the regions exposed to the light has an increase in crosslinking density. The regions without exposure remain its crosslinking density. Thus, a crosslinking density gradient forms in the stromal layer of the corneal. Different crosslinking densities cause a hydrature distribution in the stromal layer, resulting in an internal stress. As the internal stress is released, the corneal curvature changes and reaches a new equilibrium. Based on this principle, the overall curvature of the corneal can be either increased or decreased. Also, the corneal curvature can be locally increased or decreased.

The photoinitiator is a type of substance that can produce reactive oxygen species under the light of specified wavelength, the produced reactive oxygen species induce the collagen of the stromal layer of the corneal to undertake the crosslinking reaction.

Preferably, the photoinitiators used in the present invention may be selected from: riboflavin, riboflavin derivatives, eosin Y, eosin Y derivatives, acriflavine, quinidine, methylene blue or erythrosine. Further preferably, the photoinitiators are riboflavin, riboflavin derivatives or eosin Y.

Preferably, when the photoinitiator is riboflavin or riboflavin derivatives, the wavelength of the light source is 320-400 nm. When the photoinitiator is selected from eosin Y, eosin Y derivatives, acriflavine, quinidine, methylene blue or erythrosine, the wavelength of the light source is 460-668 nm.

As particularly preferable embodiments of the invention, when the photoinitiator is riboflavin or riboflavin sodium phosphate, the specified light wavelength is 365-370 nm. When the photoinitiator is chosen from riboflavin or riboflavin sodium phosphate, the photoinitiator has shielding effect, absorbing ultraviolet ray at the light wavelength of 365-370 nm and preventing the light's damages to corneal endothclium, lens, and retina. when the photoinitiator is eosin Y, the wavelength of the light source is 550-560 nm.

Preferably, the photoinitiator is 0.01% to 0.5% by weight relative to the weight of the total composition. Preferably, the photoinitiator concentration is between 0.05% and 0.5%.

Preferably, the solution also includes a penetrating agent. The penetrating agent may facilitate the photoinitiator to penetrate the corneal epithelium and reach the substantia propria layer.

More preferably, the penetrating agent may be chosen from EDTA, EDTA sodium, EDTA potassium, polysorbate 80, trometamol, azone, benzoyl hydroxylamine chloride, cetylpyridinium chloride, lauric acid, cetyl trimethyl ammonium chloride, polyoxyethylene, sodium salicylate or taurocholic acid. The penetrating agent is used in this invention in an amount ranging from 0.01% to 5% by weight relative to the total solution.

Preferably, the solution is dextran solution in an amount ranging from 0.01% to 20% by weight relative to the total solution.

Preferably, the irradiation time of the local area is 0.1-5 minutes and the power of the light of the specified wavelength is 0.1-5 mW/cm$^2$.

The present invention also discloses an apparatus for the digital corneal crosslinking. The apparatus comprises a light source, a digital micromirror device and a computer with graphic software. The digital micromirror device is used to adjust the irradiation area and irradiation time. The computer controls the digital micromirror device through graphic software.

Advantageously, the apparatus for the digital corneal crosslinking also includes an eye tracking/positioning device and a corneal topography acquisition device. The eye tracker is a device for measuring eye positions and eye movement, transferring the information to the computer. The corneal topography acquisition device sends the corneal curvature and thickness in real-time to the computer. The computer adjusts the irradiation area and irradiation time according to the feedback from the eye tracker and the corneal topography acquisition device.

Under the control of the computer graphic software, the digital micromirror device of the apparatus can adjust the light output including exposure pattern and time.

The graphic software can be chosen from CAD, Adobe Illustrator or Photoshop in order to control the digital micromirror device.

The light source is preferably integrated light emitting diodes of different wavelengths.

The eye tracking/positioning device and corneal topography acquisition device are the feedback adjustment system of the apparatus. The eye tracking/positioning device can capture minor movements of the eyeball and send the information to the computer, and the graphic software can then accordingly fine-tune the output light pattern through the digital micromirror device. The corneal topography acquisition device can send the corneal parameters such as curvature and thickness to the controlling computer in real time, so as to monitor and predict the curvature change trend.

Compared with the existing technology, the benefits of the present invention are:
(1) The present invention discloses a digital corneal crosslinking method to adjust the corneal curvature in a much lower invasive way and can accurately adjust corneal curvature radius, and can provide an all new method to treat myopia, hyperopia and astigmatism.
(2) The apparatus disclosed in this invention can effectively implement the digital corneal crosslinking process.

EMBODIMENTS OF THE INVENTION

The present invention is to further explain with reference to the following embodiments. However, the protection scope of the present invention is not limited to the scope expressed in these embodiments.

Figure 1:
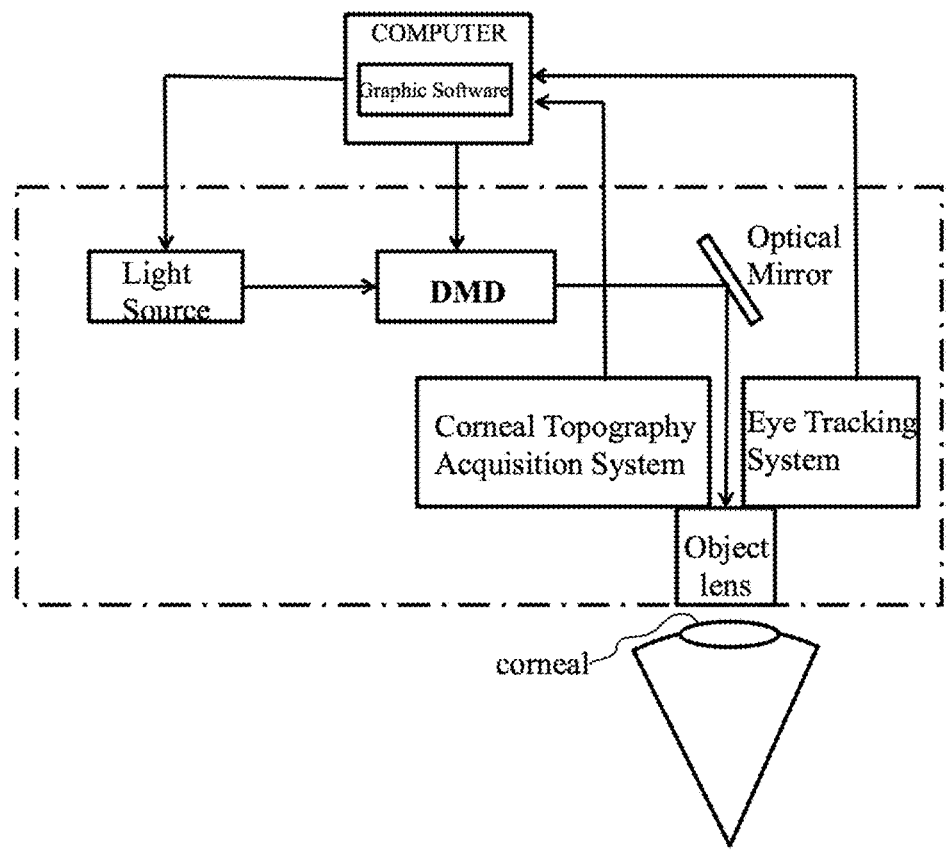
FIG. 1 is the schematic representation of the apparatus for the digital corneal crosslinking.

FIG. 1 shows the schematic representation of the apparatus for the digital corneal crosslinking comprising: a light source, a digital micromirror device, an optical mirror, objective lens, a control computer, an eye tracking/positioning device, and a corneal topography acquisition device.

The light source, digital micromirror device, optical mirror and objective mirror are on the same optical path, belonging to the optical system of the apparatus. The light irradiates the cornea through this optical path.

The control computer is installed with the graphics software (CAD) that can control the digital micromirror device so as to transfer the light source into an area light with specific pattern.

The eye tracking/positioning device and corneal topography acquisition device are connected to the control computer respectively, belonging to the feedback adjustment system of the apparatus. The eye tracking/positioning device can capture minor movement of the eyeball and send the information to the computer, and the graphic software can then accordingly fine-tune the output light pattern through the digital micromirror device. The corneal topography acquisition device can send the corneal parameters such as curvature and thickness to the control computer in real time, so as to monitor and predict the curvature change trend.

Advantageously, the digital micromirror device selects the digital micromirror device from Texas Instruments Inc., the eye tracking/positioning device selects ViewPoint Eye Tracker Systems, the corneal topography acquisition device selects OCULUSPENTCAM three-dimensional Eye analyzer.

Example 1

Figure 2:
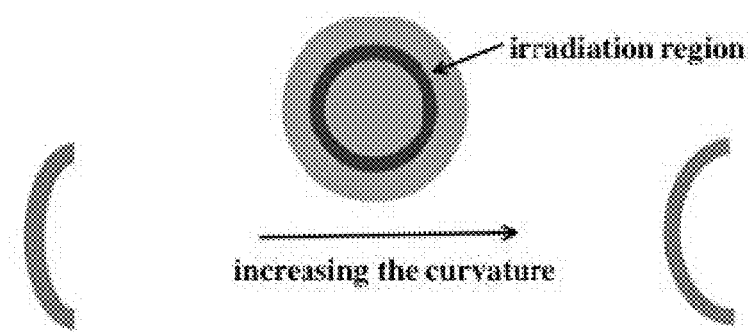
FIG. 2 is the schematic diagram of increasing the corneal curvature of embodiment 1.

The epithelial tissue of an area of 7 mm diameter in the middle of the cornea was removed after superficial anesthesia. A dextran solution of 200 g/L with 1 g/L riboflavin was dropped to corneal surface in batches. The location of the riboflavin diffused into the corneal surface was observed by cobalt blue light of a slit lamp. Digital corneal crosslinking device was used to selectively irradiate the local area of the cornea. The light's wavelength is 365 nm, the irradiation area is shown in FIG. 2, the light power is 1.2 mW/cm$^2$, irradiation time is 5 minutes.

During irradiation process, a photoinitiator solution and superficial anesthesia were used to wash the corneal surface in phases. Antibiotic eye formulations were applied to the eye and corneal contact lens were used until the corneal epithelium was healed. As shown in FIG. 2, the corneal surface curvature increased.

Example 2

The epithelial tissue of an area of 7 mm diameter in the middle of the cornea was removed after superficial anesthesia. A dextran solution of 200 g/L with 1 g/L riboflavin sodium phosphate was dropped to corneal surface in batches. The location of the riboflavin diffused into the corneal surface was observed by cobalt blue light of a slit lamp. Digital corneal crosslinking device was used to selectively irradiate the local area of the cornea. The light's wavelength is 365 nm, the irradiation area is the same like that in example 1, the light power is 1.2 mW/cm$^2$, irradiation time is 5 minutes.

During irradiation process, a photoinitiator solution and superficial anesthesia were used to wash the corneal surface in phases. Antibiotic eye formulations were applied to the eye and corneal contact lens were used until the corneal epithelium was healed. The corneal surface curvature was the same as example 1.

Example 3

Figure 3:
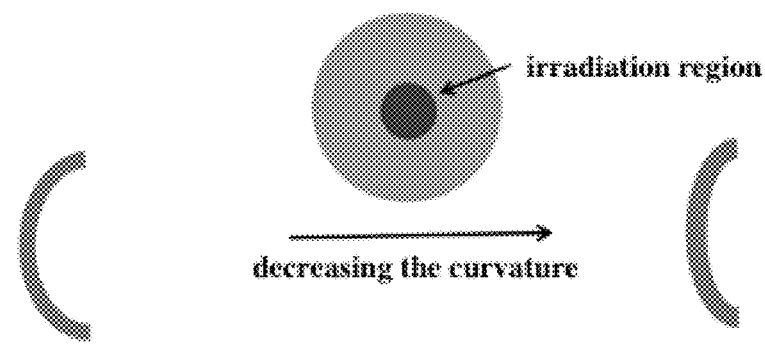
FIG. 3 is the schematic diagram of decreasing the corneal curvature of embodiment 2.

The epithelial tissue of an area of 5-9 mm diameter in the middle of the cornea was removed after superficial anesthesia. A dextran solution of 200 g/L with 1 g/L eosin Y was dropped to corneal surface in batches. The location of the eosin Y diffused into the corneal surface was observed by cobalt blue light of a slit lamp. Digital corneal crosslinking device was used to selectively irradiate the local area of the cornea. The light's wavelength is 550 nm, the irradiation area is shown in FIG. 3, the light power is 1.2 mW/cm$^2$, irradiation time is 5 minutes.

During irradiation process, the eosin Y solution and superficial anesthesia were used to wash the corneal surface in phases. Antibiotic eye formulations were applied to the eye and corneal contact lens were used until the corneal epithelium was healed. As shown in FIG. 3, the corneal surface curvature decreased.

Example 4

Figure 4:
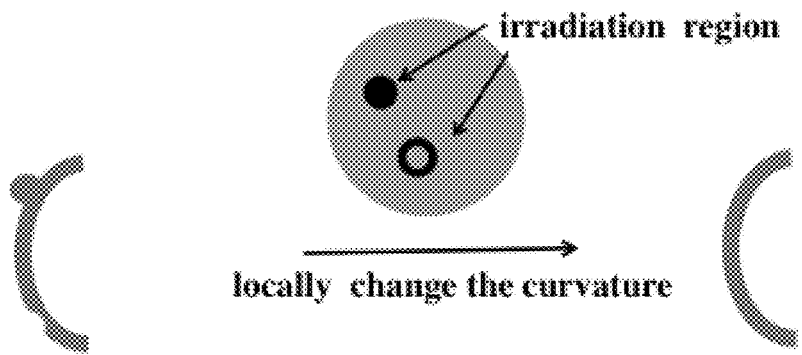
FIG. 4 is the schematic diagram of adjusting the local corneal curvature of embodiment 3.

The epithelial tissue of the cornea was removed and a dextran solution of 200 g/L with 1 g/L riboflavin was dropped to corneal surface in batches. The location of the riboflavin diffused into the corneal surface was observed by cobalt blue light of a slit lamp. Digital corneal crosslinking device was used to selectively irradiate the local area of the cornea. The light's wavelength is 365 nm, the irradiation area is shown in FIG. 4, the light power is 1.2 mW/cm$^2$, irradiation time is 5 minutes.

During irradiation process, a photoinitiator solution and superficial anesthesia were used to wash the corneal surface in phases. Antibiotic eye formulations were applied to the eye and corneal contact lens were used until the corneal epithelium was healed. The corneal curvature was locally changed as shown in FIG. 4.

Example 5

The epithelial tissue of the cornea was kept intact and a dextran solution of 200 g/L with 1.5 g/L EDTA sodium and 1.5 g/L riboflavin was dropped to corneal surface in batches. The location of the riboflavin diffused into the corneal surface was observed by cobalt blue light of a slit lamp. Digital corneal crosslinking device was used to selectively irradiate the local area of the cornea. The light's wavelength is 365 nm, the irradiation area is the same as example 1, the light power is 1.2 mW/cm$^2$, irradiation time is 10 minutes.

During irradiation process, a photoinitiator solution and superficial anesthesia were used to wash the corneal surface in phases. Antibiotic eye formulations were applied to the eye and corneal contact lens were used until the corneal epithelium was healed. The result was the same as example 1.

The invention claimed is:

1. A method of digitally adjusting a corneal curvature of an eye in a subject, the method comprising the steps of: dropping a composition comprising a photoinitiator compound to the corneal stromal of the subject, locally irradiating the cornea by utilizing a digital micromirror device controlled by graphic software in a computer, whereby the corneal curvature is altered, wherein local irradiation area and time on the corneal is determined through biomechanical simulation by establishing a dynamic model of crosslinking traction between the photoinitiator and the corneal stromal under irradiation and determining a relation between the local irradiation time and crosslinking density, wherein a corneal biomechanics analyzer is used to obtain biomechanical data including corneal thickness, intraocular pressure to set up a mechanical model, wherein finite element analysis is applied to obtain an internal stress distribution for a certain curvature change and obtain a crosslinking density distribution, wherein the digital micromirror device is used to adjust the local irradiation area and time, wherein the method utilizes an eye tracking/positioning device and a corneal topography acquisition device, and wherein the eye tracker is a device for measuring eye ball movement, transferring information to the computer; the corneal topography acquisition device sends the corneal curvature and thickness in real-time to the computer; and the computer adjusts the irradiation area and irradiation time according to the feedback from the eye tracker and the corneal topography acquisition device.

2. The method of claim 1, wherein the photoinitiator is selected from riboflavin, riboflavin derivatives, eosin Y, eosin Y derivatives, acriflavine, quinidine, methylene blue, or erythrosine.

3. The method of claim 2, wherein when the photoinitiator is riboflavin or riboflavin derivatives, wavelength of light is 320-400 nm; and wherein when the photoinitiator is eosin Y, eosin Y derivatives, acriflavine, quinidine, methylene blue and erythrosine, the wavelength is 460-668 nm.

4. The method of claim 1, wherein the amount of the photoinitiator ranges from 0.01 to 0.5% by weight.

5. The method of claim 1, wherein the composition additionally contains an assisting penetrating agent.

6. The method of claim 5, wherein the penetrating agent is selected from polysorbate 80, trometamol, azone, benzoyl hydroxylamine chloride, cetylpyridinium chloride, lauric acid, cetyl trimethyl ammonium chloride, polyoxyethylene, sodium salicylate, taurocholic acid, or a combination thereof; and the amount of which ranges from 0.01 to 5% by weight.

7. The method of claim 1, wherein the composition contains dextran; and the amount of which ranges from 0.01 to 20% by weight.

8. The method of claim 1, wherein the light irradiation time ranges from 0.1 to 5 min; the power of the light ranges from 0.1 to 5 mW/cm$^2$.

9. The method of claim 2, wherein the amount of the photoinitiator ranges from 0.01 to 0.5% by weight.

10. A method of digitally adjusting a corneal curvature of an eye in a subject, the method comprising the steps of: dropping a composition comprising a photoinitiator compound to the corneal stromal of the subject, locally irradiating the corneal by utilizing a digital micromirror device controlled by graphic software in a computer, whereby the corneal curvature is altered, wherein local irradiation area and time on the corneal is determined through biomechanical simulation by establishing a dynamic model of crosslinking traction between the photoinitiator and the corneal stromal under irradiation and determining a relation between the local irradiation time and crosslinking density, wherein a corneal biomechanics analyzer is used to obtain biomechanical data including corneal thickness, intraocular pressure to set up a mechanical model, wherein finite element analysis is applied to obtain an internal stress distribution for a certain curvature change and obtain a crosslinking density distribution, wherein the digital micromirror device is used to adjust the local irradiation area and time, wherein the method utilizes an eye tracking/positioning device and a corneal topography acquisition device, and wherein the eye tracker is a device for measuring eye ball movement, transferring information to the computer; the corneal topography acquisition device sends the corneal curvature and thickness in real-time to the computer; and the computer adjusts the irradiation area and irradiation time according to the feedback from the eye tracker and the corneal topography acquisition device, wherein when the photoinitiator is riboflavin or riboflavin derivatives, wavelength of light is 320-400 nm; and wherein when the photoinitiator is eosin Y, eosin Y derivatives, acriflavine, quinidine, methylene blue and erythrosine, the wavelength is 460-668 nm, wherein the composition additionally contains an assisting penetrating agent, wherein the penetrating agent is selected from polysorbate 80, trometamol, azone, benzoyl hydroxylamine chloride, cetylpyridinium chloride, lauric acid, cetyl trimethyl ammonium chloride, polyoxyethylene, sodium salicylate, taurocholic acid, or a combination thereof; and the amount of which ranges from 0.01 to 5% by weight.

* * * * *